United States Patent
Qian

(10) Patent No.: US 11,535,590 B2
(45) Date of Patent: Dec. 27, 2022

(54) SULFONIUM SALT PHOTOINITIATOR, PREPARATION METHOD THEREFOR, PHOTOCURABLE COMPOSITION COMPRISING SULFONIUM SALT PHOTOINITIATOR, AND USE THEREOF

(71) Applicants: CHANGZHOU TRONLY NEW ELECTRONIC MATERIALS CO., LTD., Changzhou (CN); CHANGZHOU TRONLY ADVANCED ELECTRONIC MATERIALS CO., LTD., Changzhou (CN)

(72) Inventor: Xiaochun Qian, Changzhou (CN)

(73) Assignees: Changzhou Tronly New Electronic Materials Co., Ltd., Changzhou (CN); Changzhou Tronly Advanced Electronic Materials Co., Ltd., Changzhou (CN)

(*) Notice: Subject to any disclaimer, the term of this patent is extended or adjusted under 35 U.S.C. 154(b) by 234 days.

(21) Appl. No.: 16/644,691

(22) PCT Filed: Aug. 27, 2018

(86) PCT No.: PCT/CN2018/102422
§ 371 (c)(1),
(2) Date: Mar. 5, 2020

(87) PCT Pub. No.: WO2019/047734
PCT Pub. Date: Mar. 14, 2019

(65) Prior Publication Data
US 2021/0363102 A1 Nov. 25, 2021

(30) Foreign Application Priority Data
Sep. 6, 2017 (CN) .......................... 201710797409.4

(51) Int. Cl.
| | | |
|---|---|---|
| *C07C 381/12* | (2006.01) | |
| *C07C 303/40* | (2006.01) | |
| *C07C 309/06* | (2006.01) | |
| *C07C 315/04* | (2006.01) | |
| *C07C 317/04* | (2006.01) | |
| *C07F 5/02* | (2006.01) | |
| *C07F 9/52* | (2006.01) | |
| *C07C 303/32* | (2006.01) | |
| *C07C 311/48* | (2006.01) | |

(52) U.S. Cl.
CPC .......... *C07C 381/12* (2013.01); *C07C 303/32* (2013.01); *C07C 303/40* (2013.01); *C07C 309/06* (2013.01); *C07C 311/48* (2013.01); *C07C 315/04* (2013.01); *C07C 317/04* (2013.01); *C07F 5/02* (2013.01); *C07F 9/52* (2013.01)

(58) Field of Classification Search
None
See application file for complete search history.

(56) References Cited

U.S. PATENT DOCUMENTS

| | | |
|---|---|---|
| 4,954,416 A | 9/1990 | Wright et al. |
| 5,102,772 A | 4/1992 | Angelo et al. |
| 5,470,994 A | 11/1995 | Saeva et al. |
| 7,560,219 B2 | 7/2009 | Liu et al. |
| 8,192,590 B1 | 6/2012 | Belfield et al. |
| 2009/0197987 A1 | 8/2009 | Hayoz et al. |
| 2009/0208872 A1 | 8/2009 | Wolf et al. |
| 2010/0022676 A1 | 1/2010 | Rogers et al. |
| 2010/0087563 A1 | 4/2010 | Hayoz et al. |
| 2010/0297540 A1 | 11/2010 | Hayoz et al. |
| 2010/0297541 A1 | 11/2010 | Hayoz et al. |
| 2010/0297542 A1 | 11/2010 | Hayoz et al. |

(Continued)

FOREIGN PATENT DOCUMENTS

| | | |
|---|---|---|
| CN | 1721498 | 1/2006 |
| CN | 101153016 | 4/2008 |

(Continued)

OTHER PUBLICATIONS

Office Action in Japanese Appln. 2020-513547, dated May 10, 2021, 7 pages (with English translation).
CN Office Action in Chinese Appln. No. 201710797409.4, dated Aug. 28, 2019, 8 pages (English translation).
International Search Report and Written Opinion in International Appln. No. PCT/CN2018/102422, dated Nov. 14, 2018, 6 pages.
Office Action in Korean application No. 10-2020-7008752, dated Jan. 24, 2022, 15 pages (with English Translation).

*Primary Examiner* — Rosalynd A Keys
(74) *Attorney, Agent, or Firm* — Fish & Richardson P.C.

(57) ABSTRACT

The present invention provides a sulfonium salt photoinitiator, a preparation method therefor, a photocurable composition comprising sulfonium salt photoinitiator, and use thereof. The sulfonium salt photoinitiator has a structure represented by formula (I). By modifying the structure of an existing sulfonium salt photoinitiator, a sulfonium salt photoinitiator having a new structure is obtained, which can exhibits a higher photosensitivity and an excellent as well as characteristics of low odor and low toxicity, when being used in a photocurable composition. This is significantly superior to existing similar photoinitiators.

formula (I)

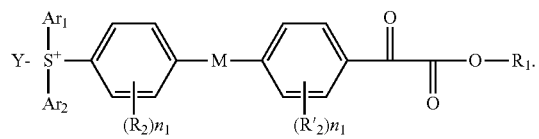

20 Claims, No Drawings

(56) References Cited

U.S. PATENT DOCUMENTS

| | | |
|---|---|---|
| 2011/0152540 A1 | 6/2011 | Nakayashiki et al. |
| 2011/0300482 A1 | 12/2011 | Suzuki et al. |

FOREIGN PATENT DOCUMENTS

| | | | | |
|---|---|---|---|---|
| CN | 102186815 | | 9/2011 | |
| CN | 103274978 | | 9/2013 | |
| CN | 105712917 | | 6/2016 | |
| CN | 108440357 | | 8/2018 | |
| EP | 1036789 A1 * | | 9/2000 | ............ B33Y 70/00 |
| EP | 1538149 | | 6/2005 | |
| JP | 2003238691 A | | 8/2003 | |
| JP | 2010505977 | | 2/2010 | |
| JP | 2011500525 | | 1/2011 | |
| JP | 2011501745 | | 1/2011 | |
| JP | 2013014534 | | 1/2013 | |
| KR | 10-2010-0074261 A | | 7/2010 | |
| WO | WO 2008/082224 | | 7/2008 | |
| WO | WO-2009047151 A1 * | | 4/2009 | ........... C07C 321/28 |
| WO | WO 2014/061062 | | 4/2014 | |

\* cited by examiner

SULFONIUM SALT PHOTOINITIATOR, PREPARATION METHOD THEREFOR, PHOTOCURABLE COMPOSITION COMPRISING SULFONIUM SALT PHOTOINITIATOR, AND USE THEREOF

CROSS-REFERENCE TO RELATED APPLICATIONS

This application is a U.S. National Phase application under 35 U.S.C. § 371 of International Patent Application No. PCT/CN2018/102422, filed on Aug. 27, 2018, which claims priority to Chinese Application No. 201710797409.4, filed on Sep. 6, 2017. The entire contents of the parent applications are hereby incorporated by reference.

TECHNICAL FIELD

The present invention relates to the field of photocuring, and particularly to a sulfonium salt photoinitiator, a preparation method therefor, a photocurable composition comprising sulfonium salt photoinitiator, and use thereof.

BACKGROUND ART

Sulfonium salts, which are used as a photoinitiator, have been well known in the art, and there are a number of literatures reporting uses of onium salt compounds as photoinitiators. However, the utilization rate of ultraviolet light sources is very low due to the limitation of the absorption wavelengths of the onium salt compounds, which always limits their applications in the field of photocuring.

In recent years, attempts have been made to improve structures of sulfonium salts so as to allow for red shift of absorption wavelengths of onium salt-based initiators. Different types of high molecular weight sulfonium salt photoinitiators have been reported and disclosed. Although the problem with absorption wavelengths of micromolecular sulfonium salt photoinitiators has been solved to some extent, the problem of poor photosensitivities of these initiators still exists. Additionally, the problems of solubilities of onium salt-based photoinitiators and toxicities and odor properties after curing are always urgent to be solved in the art.

SUMMARY OF THE INVENTION

A main object of the present invention is to provide a sulfonium salt photoinitiator, a preparation method therefor, a photocurable composition comprising sulfonium salt photoinitiator, and use thereof, to solve problems that existing photoinitiators have poor light sensitivity and toxic or odorous gas would be generated.

In order to achieve the object described above, according to an aspect of the present invention, there is provided a sulfonium salt photoinitiator, wherein the sulfonium salt photoinitiator has a structure represented by formula (I):

formula (I)

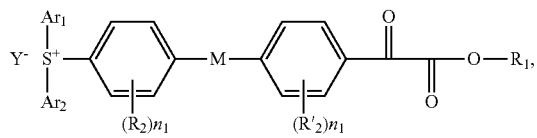

wherein $Ar_1$ and $Ar_2$ are each independently selected from an aryl group or a substituted aryl group;

$R_1$ represents a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

$R_2$ and $R_2'$ are each independently selected from a $C_1$ to $C_{20}$ linear or branched alkyl group, a $C_3$ to $C_{20}$ cycloalkyl group, or a $C_1$ to $C_{10}$ alkyl group substituted with a $C_3$ to $C_8$ cycloalkyl group, and $n_1$ and $n_2$ each independently represent an integer of 0 to 4;

M is selected from a single bond, O, S,

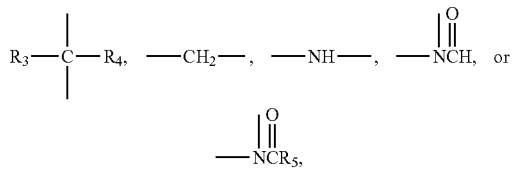

and $R_3$, $R_4$, and $R_5$ are each independently selected from organic substituents, respectively;

$Y^-$ represents an inorganic anion or an organic anion.

Furthermore, $R_1$ represents a $C_1$ to $C_{20}$ linear or branched alkyl group. Preferably, M represent O or S. Preferably, $R_2$ and $R_2'$ are each independently selected from $C_1$ to $C_5$ linear or branched alkyl groups.

Furthermore, $Ar_1$ and $Ar_2$ are each independently selected from

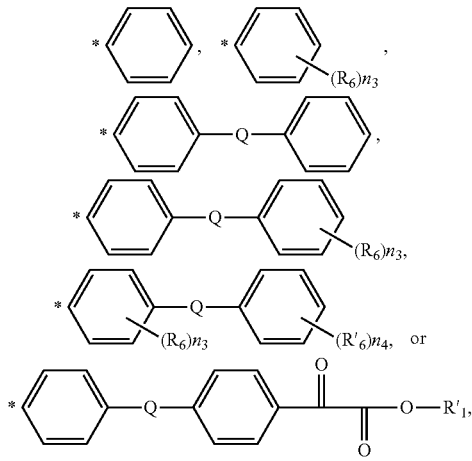

wherein $R_6$ and $R_6'$ are each independently selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group, and $n_3$ and $n_4$ are each independently selected from an integer of 1 to 4; $R_1'$ is selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group; Q is selected from a single bond, O, S,

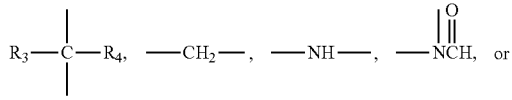

and $R_3$, $R_4$, and $R_5$ are each independently selected from organic substituents, respectively; and preferably, Q represents O or S.

Furthermore, $Y^-$ represents $X^-$, $ClO_4^-$, $CN^-$, $HSO_4^-$, $CF_3COO^-$, $(BX_4)^-$, $(SbX_6)^-$, $(AsX_6)^-$, $(PX_6)^-$, $Al[OC(CF_3)_3]_4^-$, a sulfonate ion, $B(C_6X_5)_4^-$, or $[(Rf)_bPF_{6-b}]^-$, wherein X is F or Cl, Rf represents an alkyl group in which ≥80% of hydrogen atoms are substituted with fluorine atoms, b represents an integer of 1 to 5, and b Rf groups are the same or different from each other.

Another aspect of the present application further provides a preparation method of the sulfonium salt photoinitiator described above, comprising:

a Friedel-Crafts reaction, wherein a raw material a having a structure represented by formula (II) and a raw material b having a structure represented by formula (III) are subjected to a Friedel-Crafts reaction to obtain an intermediate A having a structure represented by formula (IV), wherein said formula (II), said formula (III), and said formula (IV) are as follows:

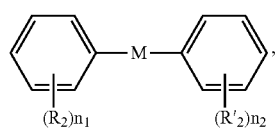
formula (II)

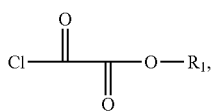
formula (III)

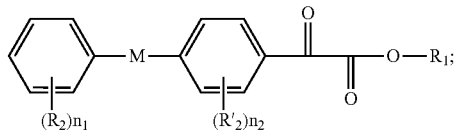
formula (IV)

a dehydration reaction, wherein the intermediate A, a first aryl compound comprising $Ar_1$, a second aryl compound comprising $Ar_2$, thionyl chloride, and aluminum chloride are subjected to a dehydration reaction to obtain an intermediate B having a structure represented by formula (V); and wherein $Ar_1$ and $Ar_2$ are each independently selected from an aryl group or a substituted aryl group, and said formula (V) is as follows:

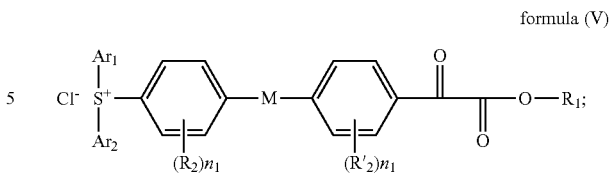
formula (V)

an ion exchange reaction, wherein the intermediate B and $Y^-$ are subjected to an ion exchange reaction to obtain the sulfonium salt photoinitiator;

wherein $R_1$ is selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

$R_2$ and $R_2'$ are each independently selected from a $C_1$ to $C_{20}$ linear or branched alkyl group, a $C_3$ to $C_{20}$ cycloalkyl group, or a $C_1$ to $C_{10}$ alkyl group substituted with a $C_3$ to $C_8$ cycloalkyl group, and $n_1$ and $n_2$ each independently represent an integer of 0 to 4;

M is selected from a single bond, O, S,

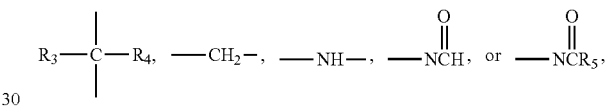

and $R_3$, $R_4$, and $R_5$ are each independently selected from organic substituents, respectively; and $Y^-$ represents an inorganic anion or an organic anion.

Furthermore, the Friedel-Crafts reaction is performed in the presence of a catalyst and an organic solvent. Preferably, the catalyst is aluminum chloride or zinc chloride.

Furthermore, the Friedel-Crafts reaction has a reaction temperature of 5 to 15° C., preferably 5 to 10° C. Preferably, the molar ratio of the raw material a, the raw material b, and the catalyst is 1:1:1.

Furthermore, the dehydration reaction has a reaction temperature of −5 to 15° C., preferably −5 to 5° C.

Another aspect of the present application further provides a photocurable composition comprising a polymerizable monomer and a photoinitiator, wherein the photoinitiator comprises the sulfonium salt photoinitiator described above.

Yet another aspect of the present application further provides use of the sulfonium salt photoinitiator described above in the field of photocuring.

By using the technical solution of the present invention, by modifying the structure of an existing sulfonium salt photoinitiator, a sulfonium salt photoinitiator having a new structure is obtained, which can exhibits a higher photosensitivity and an excellent as well as characteristics of low odor and low toxicity, when being used in a photocurable composition. This is significantly superior to existing similar photoinitiators.

DESCRIPTION OF EMBODIMENTS

It is to be indicated that Examples in the present application and features in the Examples may be combined with each other without being conflicted. This invention will be illustrated in detail in conjunction with Examples below.

As described in the background art, there are problems that existing photoinitiators have poor light sensitivity and toxic or odorous gas would be generated. In order to solve the technical problem described above, the present application provides a sulfonium salt photoinitiator, wherein the sulfonium salt photoinitiator has a structure represented by formula (I):

formula (I)

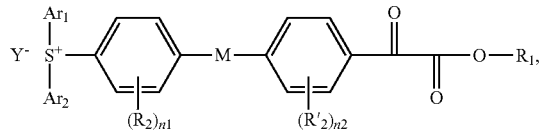

wherein $Ar_1$ and $Ar_2$ are each independently selected from an aryl group or a substituted aryl group;

$R_1$ represents a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

$R_2$ and $R_2'$ are each independently selected from a $C_1$ to $C_{20}$ linear or branched alkyl group, a $C_3$ to $C_{20}$ cycloalkyl group, or a $C_1$ to $C_{10}$ alkyl group substituted with a $C_3$ to $C_8$ cycloalkyl group, and $n_1$ and $n_2$ each independently represent an integer of 0 to 4;

M is selected from a single bond, O, S,

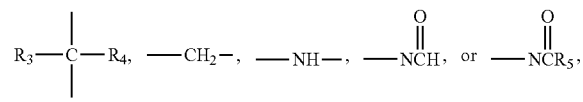

and $R_3$, $R_4$, and $R_5$ are each independently selected from organic substituents, respectively such as a $C_1$ to $C_8$ alkyl group, a $C_6$ to $C_{10}$ aryl group, and the like;

$Y^-$ represents an inorganic anion or an organic anion.

Preferably, in order to improve the stability of the sulfonium salt described above, $R_1$ is selected from $C_1$ to $C_{20}$ linear or branched alkyl groups. M is selected from O or S.

$R_2$ and $R_2'$ are each independently selected from $C_1$ to $C_5$ linear or branched alkyl groups.

By modifying the structure of an existing sulfonium salt photoinitiator, a sulfonium salt photoinitiator having a new structure is obtained, which can exhibits a higher photosensitivity and an excellent as well as characteristics of low odor and low toxicity, when being used in a photocurable composition. This is significantly superior to existing similar photoinitiators.

Preferably, $Ar_1$ and $Ar_2$ are each independently selected from

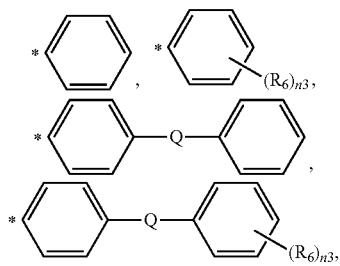

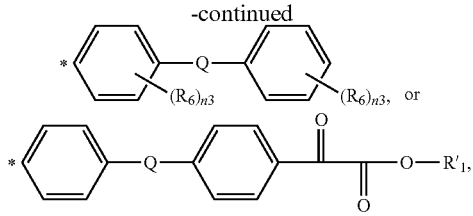

$R_6$ and $R_6'$ are each independently selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group, and $n_3$ and $n_4$ are each independently selected from an integer of 1 to 4;

$R_1'$ is selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

Q is selected from a single bond, O, S,

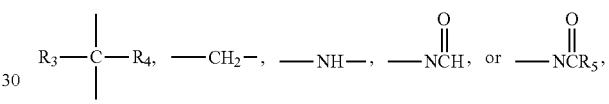

and $R_3$, $R_4$, and $R_5$ are each independently selected from organic substituents, respectively; and $Y^-$ represents an inorganic anion or an organic anion. Preferably, Q is selected from O or S.

Preferably, $Y^-$ represents $X^-$, $ClO_4^-$, $CN^-$, $HSO_4^-$, $CF_3COO^-$, $(BX_4)^-$, $(SbX_6)^-$, $(AsX_6)^-$, $(PX_6)^-$, Al $[OC(CF_3)_3]_4^-$, a sulfonate ion, $B(C_6X_5)_4^-$, or $[(Rf)PF_{6-b}]^-$, wherein X is F or Cl, Rf represents an alkyl group in which ≥80% of hydrogen atoms are substituted with fluorine atoms, b represents an integer of 1 to 5, and b Rf groups are the same or different from each other. For example, when Rf represents a propyl group, at least 4 H atoms in the propyl group are substituted with F atoms.

Another aspect of the present application further provides a preparation method of the sulfonium salt photoinitiator described above, comprising:

a Friedel-Crafts reaction, wherein a raw material a having a structure represented by formula (II) and a raw material b having a structure represented by formula (III) are subjected to a Friedel-Crafts reaction to obtain an intermediate A having a structure represented by formula (IV), wherein formula (II), formula (III), and formula (IV) are as follows:

formula (II)

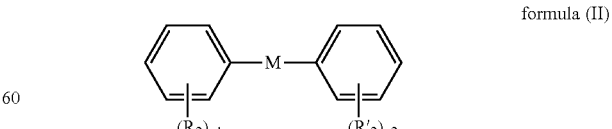

formula (III)

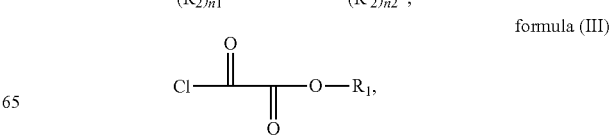

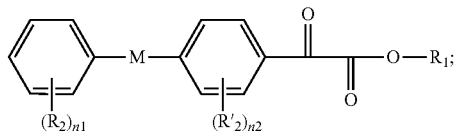

formula (IV)

a dehydration reaction, wherein the intermediate A, a first aryl compound comprising $Ar_1$, a second aryl compound comprising $Ar_2$, thionyl chloride, and aluminum chloride are subjected to a dehydration reaction to obtain an intermediate B having a structure represented by formula (V); wherein $Ar_1$ and $Ar_2$ are each independently selected from an aryl group or a substituted aryl group, and formula (V) is as follows:

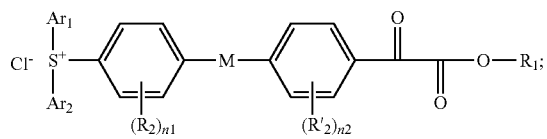

formula (V)

and an ion exchange reaction, wherein the intermediate B and $Y^-$ are subjected to an ion exchange reaction to obtain the sulfonium salt photoinitiator;

wherein $R_1$ is selected from a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

M is selected from a single bond, O, S,

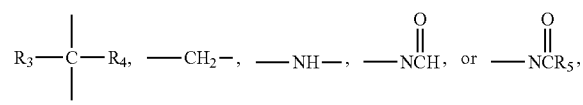

and $R_3$, $R_4$, and $R_5$ are each independently selected from organic substituents, respectively; and $R_2$ and $R_2'$ are each independently selected from a $C_1$ to $C_{20}$ linear or branched alkyl group, a $C_3$ to $C_{20}$ cycloalkyl group, or a $C_1$ to $C_{10}$ alkyl group substituted with a $C_3$ to $C_8$ cycloalkyl group, $n_1$ and $n_2$ each independently represent an integer of 0 to 4;

$Y^-$ represents an inorganic anion or an organic anion.

All of the raw materials used in the preparation method described above are compounds which are known in the prior art, commercially available, or conveniently prepared by known synthetic methods. On the basis of knowing the idea of synthesis disclosed in the present invention, specific reaction conditions will be easily determined by the person skilled in the art.

Preferably, the Friedel-Crafts reaction is performed in the presence of a catalyst and an organic solvent.

The type of the organic solvent is not particularly limited, as long as raw materials for reaction can be dissolved and there is no adverse influence on the reaction, and dichloromethane, dichloroethane, benzene, toluene, and the like are preferable. The ratio of the raw materials for reaction will be easily determined by those skilled in the art. Preferably, the catalyst is aluminum chloride or zinc chloride.

Preferably, the Friedel-Crafts reaction has a reaction temperature of 5 to 15° C., preferably 5 to 10° C. Preferably, the molar ratio of the raw material a, the raw material b, and the catalyst is 1:1:1.

Preferably, the dehydration reaction has a reaction temperature of −5 to 15° C., preferably −5 to 5° C. The ratio of the raw materials for reaction will be easily determined by those skilled in the art. Preferably, the molar ratio of the intermediate a, $Ar_1$, $Ar_2$, $SOCl_2$, and aluminum chloride or zinc chloride is 1:1:1:1:2. In this reaction, the intermediate a, the first aryl compound containing $Ar_1$, and the second aryl compound containing $Ar_2$ may be three different compounds, or two of the three compounds are the same, or all of the three compounds are the same.

In the preparation method described above, the ion exchange reaction is preferably performed in a solvent. The type of the solvent is not particularly limited, as long as the solvent used as a reaction support does not have an adverse effect on the reaction. This reaction may be performed at room temperature.

This application will be further described in detail in conjunction with specific Examples below. These Examples may not be construed as limiting the scope sought to be protected by the present application.

PREPARATION EXAMPLES

Example 1

Step (1): Preparation of Intermediate a1

93.1 g of diphenyl sulfide, 61.3 g of methyl oxalyl chloride, and 150 mL of dichloromethane were added to a 500 mL four-neck flask and the reaction system described above was cooled with an ice-water bath, while the temperature was controlled to be about 5° C. 83.3 g of aluminum chloride was then added to the reaction system described above in batches for about 1 h. Stirring was continued for 2 h, and liquid phase tracking was performed until the reaction was complete.

A dichloromethane solution containing a product was poured into 500 g of ice water with continuous stirring, and a dichloromethane layer was separated and washed with water. The dichloromethane solution of the product was then treated in a manner of rotary evaporation to obtain 129.4 g of a light yellow solid, which was an intermediate a1, with a yield of 95 wt % and an HPLC purity of 98 wt %. The synthetic scheme was as follows: PGP-3

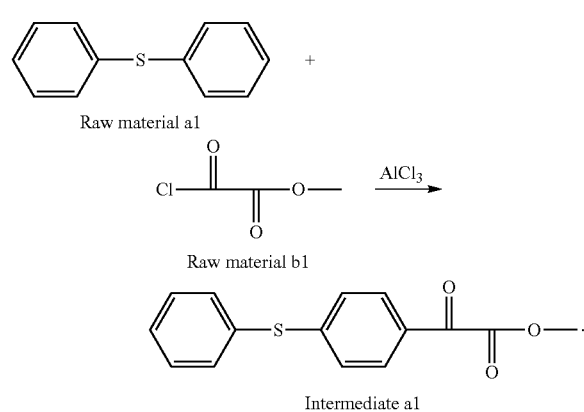

The structure of the intermediate product was determined by hydrogen nuclear magnetic resonance spectroscopy and mass spectrometry, and the specific characterization result was as follows:

$^1$H-NMR (CDCl$_3$, 500 MHz): 3.6462 (3H, s), 7.0708-7.6325 (9H, m).

MS (m/Z): 273 (M+H)$^+$.

Step (2): Preparation of Intermediate b1

81.7 g of the intermediate a1, 100 mL of dichloromethane, and 16.7 g of aluminum chloride were added to a 500 mL four-neck flask and the reaction system described above was stirred under a condition of an ice-water bath, while the temperature was controlled to be about 0° C. 11.9 g of thionyl chloride was then dropped into the reaction system described above for about 1 h. Liquid phase tracking was performed on the reaction until the amount of the raw materials did not change any more. Next, 100 mL of iced deionized water was slowly dropped into the reaction system described above to separate a dichloromethane layer, and an aqueous layer is an aqueous solution of the intermediate b1.

The synthetic scheme was as follows:

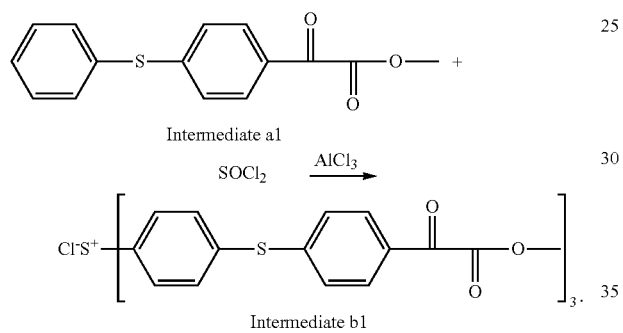

Step (3): Preparation of Compound 1, i.e., Product of Interest 18.5 g of KPF$_6$ solid was added to the aqueous solution of the intermediate b1 described above to perform ion exchange, and deionized water was appropriately replenished with stirring. As the KPF$_6$ solid dissolved, a product of interest (i.e., compound 1) gradually precipitated, and was filtered, recrystallized with methanol, and dried to obtain 66.6 g of a white solid with an HPLC purity of 99 wt %.

The synthetic scheme was as follows:

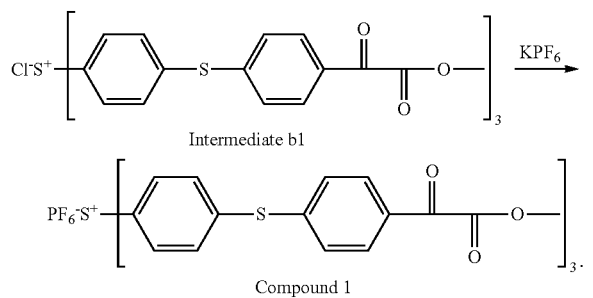

The structure of the product of interest was determined by hydrogen nuclear magnetic resonance spectroscopy and mass spectrometry, and the specific characterization result was as follows:

$^1$H-NMR (MeOD, 500 MHz): 3.6705 (12H, s), 7.0984-7.1975 (12H, m), 7.3708-7.3948 (6H, d), 7.5704-7.6241 (6H, d).

MS (m/Z): 845 (M)$^+$.

Example 2

Step (1): Preparation of Intermediate a2

85.1 g of diphenyl ether, 68.3 g of ethyl oxalyl chloride, and 150 mL of dichloromethane were added to a 500 mL four-neck flask and the reaction system described above was cooled with an ice-water bath, while the temperature was controlled to be about 5° C. 83.3 g of aluminum chloride was then added to the reaction system described above in batches for about 1 h. Stirring was continued for 2 h, and liquid phase tracking was performed until the reaction was complete.

A dichloromethane solution containing a product was poured into 500 g of ice water with continuous stirring, and a dichloromethane layer was separated and washed with water. The dichloromethane solution of the product was then treated in a manner of rotary evaporation to obtain 125.7 g of a light yellow solid, which was an intermediate a2, with a yield of 93 wt % and an HPLC purity of 98%.

The synthetic scheme was as follows:

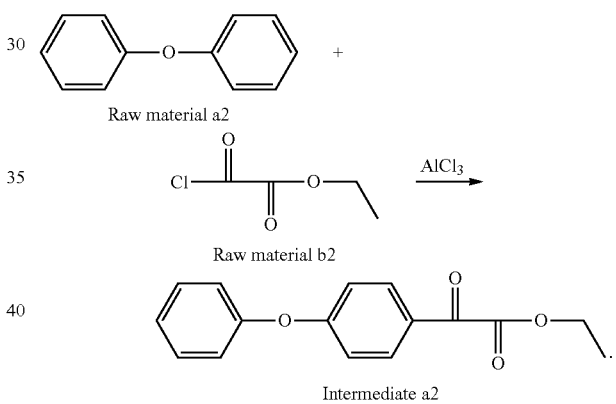

The structure of the intermediate product was determined by hydrogen nuclear magnetic resonance spectroscopy and mass spectrometry, and the specific characterization result was as follows:

$^1$H-NMR (CDCl$_3$, 500 MHz): 1.2965-1.3301 (3H, t), 4.1649-4.2005 (2H, m), 7.0038-7.7592 (9H, m).

MS (m/Z): 271 (M+H)$^+$.

Step (2): Preparation of Intermediate b2

27.0 g of the intermediate a2, 15.6 g of benzene, 100 mL of dichloromethane, and 16.7 g of aluminum chloride were added to a 500 mL four-neck flask and the reaction system described above was stirred under a condition of an ice-water bath, while the temperature was controlled to be about 0° C. 11.9 g of thionyl chloride was then dropped into the reaction system described above for about 1 h. Liquid phase tracking was performed on the reaction until the amount of the raw materials did not change any more. Next, 100 mL of iced deionized water was slowly dropped into the reaction system described above to separate a dichloromethane layer, and an aqueous layer is an aqueous solution of the intermediate b2. The synthetic scheme was as follows:

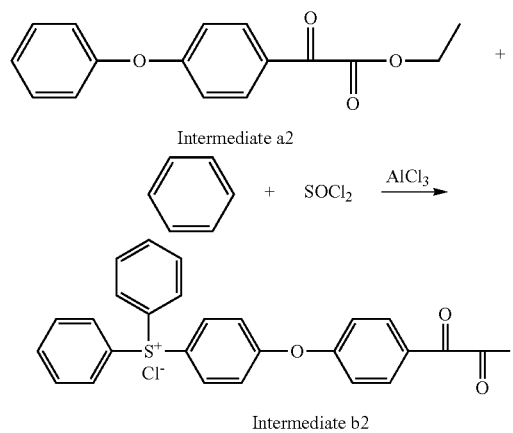

Intermediate a2

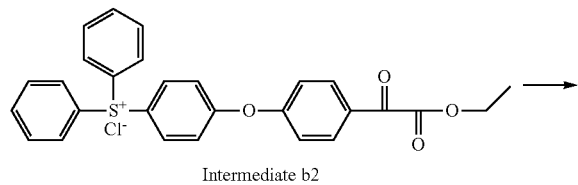

Intermediate b2

Step (3): Preparation of Compound 2, i.e., Product of Interest 18.5 g of NaC$_4$F$_9$SO$_3$ solid was added to the aqueous solution of the intermediate b2 described above to perform ion exchange, and deionized water was appropriately replenished with stirring. As the NaC$_4$F$_9$SO$_3$ solid dissolved, a product of interest (i.e., compound 2) gradually precipitated, and was filtered, recrystallized with methanol, and dried to obtain 50.5 g of a white solid with an HPLC purity of 99 wt %. The synthetic scheme was as follows:

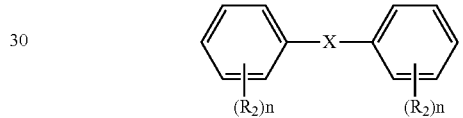

Intermediate b2

→

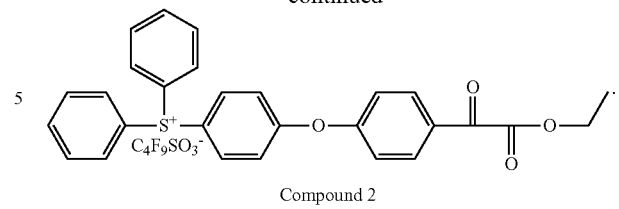

Compound 2

The structure of the product of interest was determined by hydrogen nuclear magnetic resonance spectroscopy and mass spectrometry, and the specific characterization result was as follows:

$^1$H-NMR (MeOD, 500 MHz): 1.2907-1.3102 (3H, t), 4.1832-4.2332 (2H, m), 6.9784-7.3343 (16H, m), 7.74886-7.7658 (2H, d).

MS (m/Z): 455 (M)$^+$.

Examples 3 to 12

With reference to the methods of Examples 1 and 2, compounds 3 to 12 as shown in Table 1 were prepared by using a raw material a ![](structure with two phenyl rings connected by X, each with (R$_2$)n substituents)

and the raw material b, alkyl oxalyl chloride, as starting materials.

The structures of the products of interest and MS (m/Z) data thereof were listed in Table 1.

TABLE 1

| Compound | Structure | MS (m/Z) |
|---|---|---|
| 3 | (SO$_2$$^-$CF$_3$)$_3$C$^-$S$^+$—[phenyl—S—phenyl—C(O)—C(O)—O—CH$_3$]$_3$ | 845 |
| 4 | [(C$_6$F$_5$)$_4$B]$^-$ S$^+$—[phenyl—S—phenyl—C(O)—C(O)—O—CH$_3$]$_3$ | 845 |
| 5 | PF$_6$$^-$S$^+$—[phenyl—S—phenyl—C(O)—C(O)—O—C$_2$H$_5$]$_3$ | 888 |
| 6 | [(CF$_3$CF$_2$)$_3$PF$_3$]$^-$S$^+$—[phenyl—S—phenyl—C(O)—C(O)—O—iPr]$_3$ | 930 |

TABLE 1-continued

| Compound | Structure | MS (m/Z) |
|---|---|---|
| 7 | 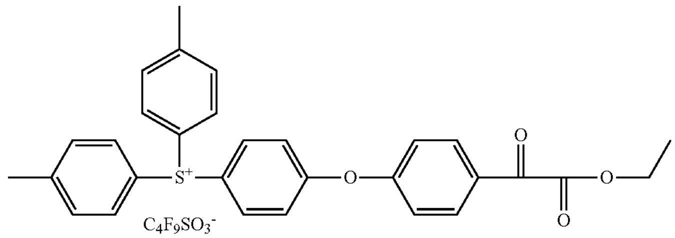 | 483 |
| 8 | 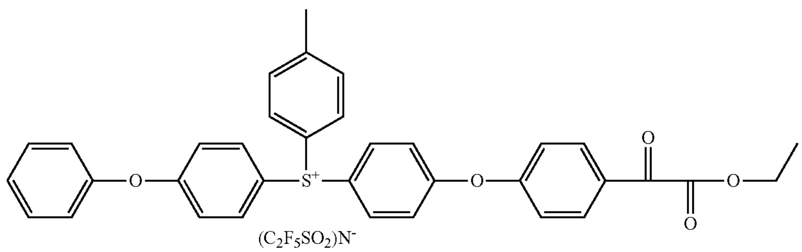 | 561 |
| 9 | 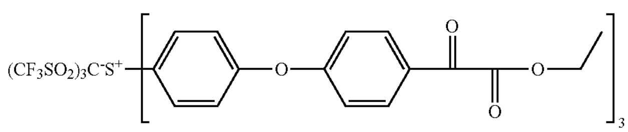 | 839 |
| 10 | 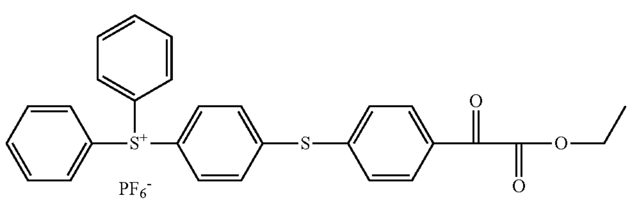 | 471 |
| 11 | 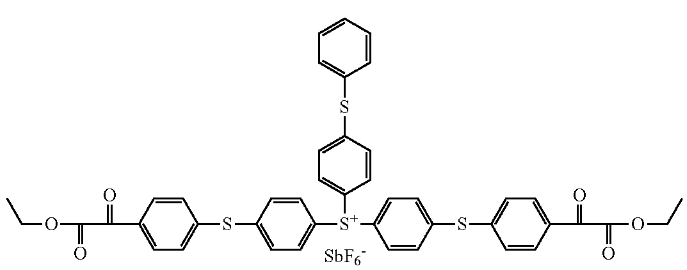 | 772 |

TABLE 1-continued

| Compound | Structure | MS (m/Z) |
|---|---|---|
| 12 | 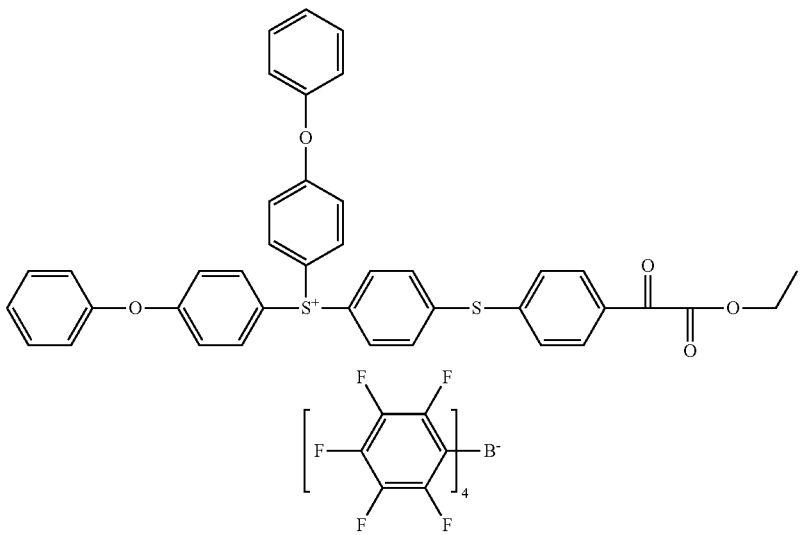 | 655 |

Photocurable Compositions

Yet another aspect of the present application further provides a photocurable composition comprising a polymerizable monomer and a photoinitiator, wherein the photoinitiator comprises the sulfonium salt photoinitiator described above.

When the above sulfonium salt photoinitiator represented by formula (I) is used in a photocurable composition, The photocurable composition described above has characteristics of high photosensitivity, excellent solubility, low odor, and low toxicity. As can be seen, the overall properties of the photocurable composition are significantly superior to those of existing similar photoinitiators.

Preferably, the photocurable composition comprises a cationic reactive compound (component A), a sulfonium salt photoinitiator represented by formula (I) (component B), and optionally a radical-type reactive compound (component C).

Preferably, the cationic reactive compound is at least one of an epoxy-containing compound or an alkenyl ether-based compound.

Preferably, the epoxy-containing compound is selected from one or more of the group consisting of a glycidyl ether-based epoxy resin, a glycidyl ester-based epoxy resin, a glycidyl amine-based epoxy resin, a linear aliphatic epoxy resin, an aliphatic epoxy resin, and an oxetane-based compound.

Preferably, the alkenyl ether-based compound is a vinyl ether-based compound.

The photocurable composition of the present invention has the advantages of high curing speed and good compatibility between respective components. The components will be illustrated in more detail below. In addition to the components A, B, and optionally C described above, organic aids and/or inorganic aids commonly used in the art may be further selectively added to the radiation-sensitive composition of the present invention according to the requirements for the applications of the products, which include, but are not limited to, pigments, leveling agents, dispersants, curing agents, surfactants, solvents, and the like, which are obvious for those skilled in the art. Additionally, in the case where the application effect of the composition is not adversely affected, other sensitizers and/or photoinitiators may also be added to the composition and used after compounding.

Preferably, one or more macromolecular or polymeric compound(s) may be further selectively added to the composition to improve the application performance of the composition in the process of use, wherein this macromolecular or polymeric compound may be a polyol, a polyester polyol, or the like.

Yet another aspect of the present application further provides use of the sulfonium salt photoinitiator described above in the field of photocuring.

When the above sulfonium salt photoinitiator represented by formula (I) is used in the field of photocuring, this initiator is significantly superior to existing similar photoinitiators since it can exhibits a higher photosensitivity and an excellent as well as characteristics of low odor and low toxicity.

Application Examples

Evaluation of Solubilities of Photoinitiators

Triphenylsulfonium salts do not have good solubilities in active diluents, and therefore current commercial triphenylsulfonium salts are all 50% propylene carbonate solutions. Several types of commonly-used cationic active diluents were selected, and the solubilities of various compounds therein were measured, respectively, which were seen in Table 2.

TABLE 2

|  | DVE-3 | Epoxy resin 6110 | DOX | POX |
|---|---|---|---|---|
| Compound 1 | >10% | >10% | >10% | >10% |
| Compound 2 | >10% | >10% | >10% | >10% |
| Compound 4 | >10% | >10% | >10% | >10% |

TABLE 2-continued

| | DVE-3 | Epoxy resin 6110 | DOX | POX |
|---|---|---|---|---|
| Compound 7 | >10% | >10% | >10% | >10% |
| Compound 11 | >10% | >10% | >10% | >10% |
| UVI6976 | <2% | <2% | <2% | <2% |
| UVI6992 | <2% | <2% | <2% | <2% |

DVE-3: triethyleneglycol divinyl ether;
Epoxy resin 6110: 3,4-epoxycyclohexylmethyl-3,4-epoxycyclohexyl carboxylate;
DOX: 3,3'-[oxybismethylene]bis[3-ethyl] oxetane;
POX: 3-ethyl-3-(phenoxymethyl) oxetane;
UVI6976: bis(4,4'-thioether triphenylsulfonium) hexafluoroantimonate;
UVI6992: phenylthiophenyl diphenylsulfonium hexafluoroantimonate.

Evaluation of Application Performances of Photocurable Compositions (1) Formulation of Photocurable Compositions The photocurable compositions below were formulated according to the formulations in Table 3.

TABLE 3

| Composition (Parts by weight) | | Example 1 | Example 2 | Example 3 | Example 4 | Example 5 | Comparative Example 1 | Comparative Example 2 | Comparative Example 3 |
|---|---|---|---|---|---|---|---|---|---|
| Photoinitiator | Compound 1 | 3 | 3 | 3 | | | | | |
| | Compound 2 | | | | 3 | | | | |
| | Compound 3 | | | | | 3 | | | |
| | UVI6976 | | | | | | 3 | 3 | 3 |
| Cationic reactive compound | Epoxy resin 6110 | 100 | 80 | 100 | 80 | 100 | 100 | 100 | 80 |
| | DOX | | 20 | | 20 | | | | 20 |
| Solvent | Solvent propylene carbonate | / | / | 2 | / | / | 2 | / | 2 |

The photocurable compositions described above were each stirred under a yellow light lamp until they became transparent and uniform, then coated on a glass plate with a coater, and dried to form a coating film with a thickness of 100 μm. Exposure was then performed in a track type exposure machine with an exposure machine model RW-UV20101 and a mercury lamp power of 300 W to obtain a cured film.

(2) Tests of Curing Properties

The shortest radiation time required for curing and film forming with a track type exposure machine was used as the curing time. The shorter the curing time was, the higher the sensitivity of the initiator was. The tests of the curing properties of the photocurable compositions prepared in Examples 1 to 5 and Comparative Examples 1 to 3 of the present application were seen in Table 4.

TABLE 4

| Example/Comparative Example | Performance Curing time (s) |
|---|---|
| Example 1 | 1 |
| Example 2 | 2S |
| Example 3 | 2S |
| Example 4 | 2S |
| Example 5 | 1S |
| Comparative Example 1 | 4S |
| Comparative Example 2 | / |
| Comparative Example 3 | 4S |

As can be seen from the Table above, the sulfonium salt-based photoinitiator described in the present invention has good solubility and has high curing speed after used in a photocuring system. It is significantly superior to the two conventional cationic photoinitiators used as comparisons, and has remarkable advantages and broad application prospects.

Those described above are merely preferred Examples of the present invention, and are not intended to limit the present invention. With respect to those skilled in the art, there may be various modifications and variations of the present invention. All of modifications, equivalent replacements, improvements, and the like, which are within the spirit and the principle of the present invention, should be encompassed in the scope protected by the present invention.

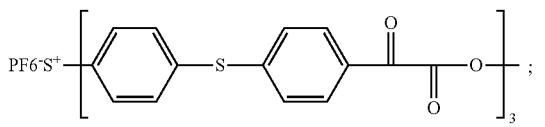

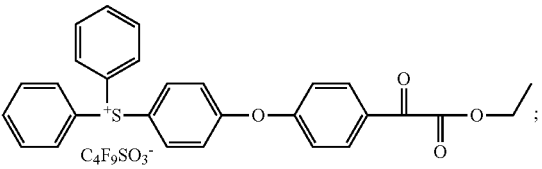

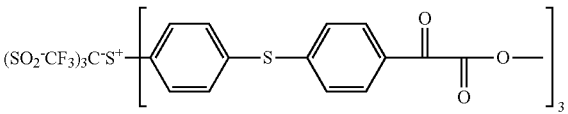

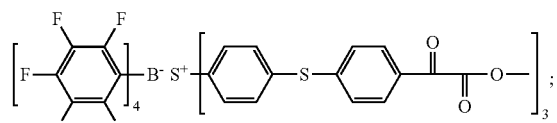

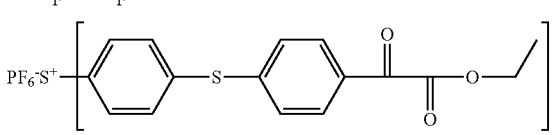

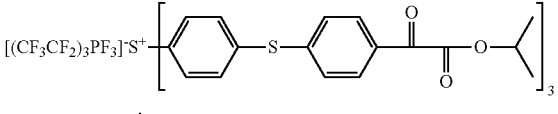

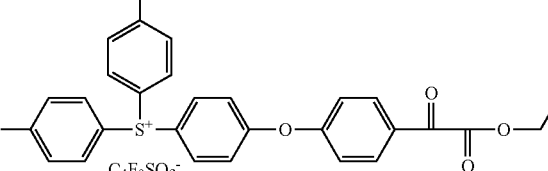

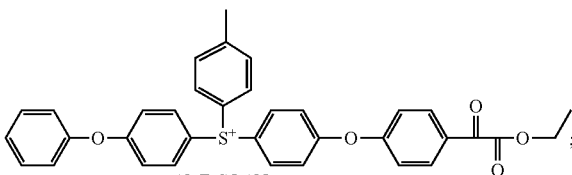

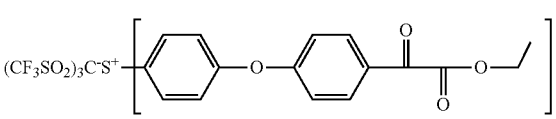

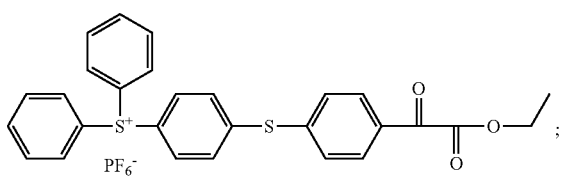

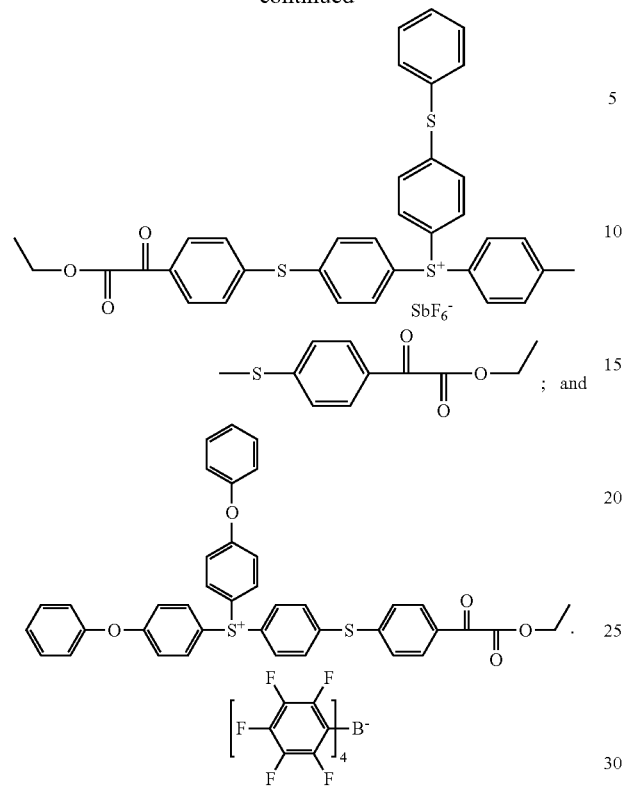

What is claimed is:

1. A sulfonium salt photoinitiator, wherein the sulfonium salt photoinitiator has a structure represented by formula (I):

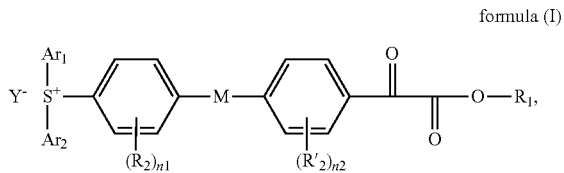

formula (I)

wherein $Ar_1$ is an aryl group or a substituted aryl group; $Ar_2$ is

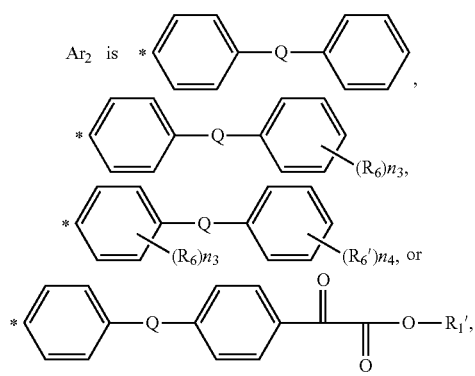

wherein $R_6$ and $R_6'$ are each independently a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_3$ to $C_{20}$ heterocyclic group, or a $C_1$ to $C_{10}$ alkyl group substituted with a C6 to C14 aryl group, and n3 and $n_4$ are each independently an integer of 0 to 4; $R_1$, is a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group; and Q is a single bond, O, S,

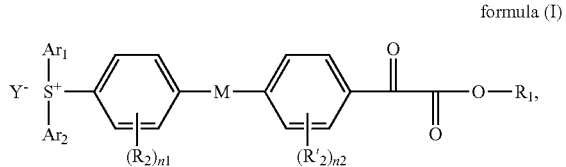

formula (I)

and $R_3$, $R_4$, and $R_5$ are each independently an organic substituent;

$R_1$ represents a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group;

$R_2$ and $R_2'$ are each independently a $C_1$ to $C_{20}$ linear or branched alkyl group, a $C_3$ to $C_{20}$ cycloalkyl group, or a $C_1$ to $C_{10}$ alkyl group substituted with a $C_3$ to $C_8$ cycloalkyl group, and $n_1$ and $n_2$ each independently represent an integer of 0 to 4;

M is a single bond, O, S,

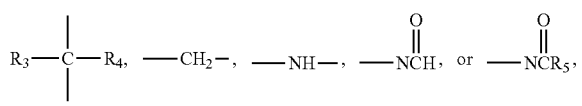

and $R_3$, $R_4$, and $R_5$ are each independently an organic substituent;

$Y^-$ represents an inorganic anion or an organic anion.

2. The sulfonium salt photoinitiator according to claim 1, wherein $R_1$ represents a $C_1$ to $C_{20}$ linear or branched alkyl group.

3. The sulfonium salt photoinitiator according to claim 1, wherein $Ar_1$ is

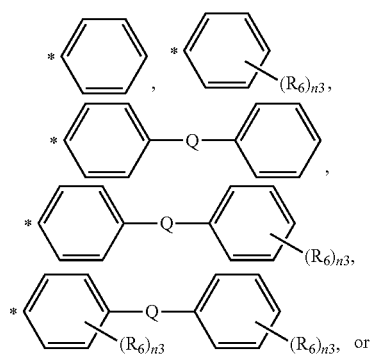

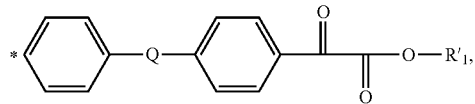

wherein $R_6$ and $R_6'$ are each independently a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a $C_6$ to $C_{14}$ aryl group, and $n_3$ and $n_4$ are each independently an integer of 1 to 4;

$R_1'$ is a $C_1$ to $C_{20}$ linear or branched alkyl group, a $C_3$ to $C_{20}$ cycloalkyl group, a $C_1$ to $C_{10}$ alkyl group substituted with a $C_3$ to $C_8$ cycloalkyl group, a $C_3$ to $C_8$ cycloalkyl group substituted with a $C_4$ to $C_{20}$ alkyl group, a $C_6$ to $C_{20}$ aryl group, a $C_2$ to $C_{20}$ heterocyclic group, or a $C_1$ to $C_{10}$ alkyl group substituted with a to $C_6$ to $C_{14}$ aryl group;

Q is a single bond, O, S,

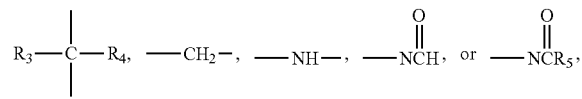

and $R_3$, $R_4$, and $R_5$ are each independently an organic substituent.

4. The sulfonium salt photoinitiator according to claim 1, wherein $Y^-$ represents $X^-$, $ClO_4^-$, $CN^-$, $HSO_4^-$, $CF_3COO^-$, $(BX_4)^-$, $(SbX_6)^-$, $(AsX_6)^-$, $(PX_6)^-$, $Al[OC(CF_3)_3]_4^-$, a sulfonate ion, $B(C_6X_5)_4^-$, or $[(Rf)_bPF_{6-b}]^-$, wherein X is F or Cl, Rf represents an alkyl group in which ≥80% of hydrogen atoms are substituted with fluorine atoms, b represents an integer of 1 to 5, and Rf groups are the same or different from each other.

5. A preparation method of the sulfonium salt photoinitiator of claim 1, wherein the preparation method comprises:

subjecting a raw material a having a structure represented by formula (II) and a raw material b having a structure represented by formula (III) to a Friedel-Crafts reaction to obtain an intermediate A having a structure represented by formula (IV), wherein formula (II), formula (III), and formula (IV) are as follows:

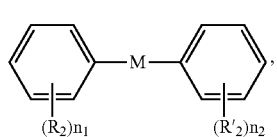

formula (II)

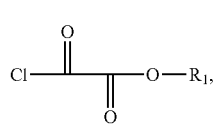

formula (III)

-continued formula (IV)

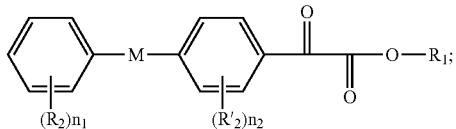

subjecting the intermediate A, a first aryl compound comprising Ar₁, a second aryl compound comprising Ar₂, thionyl chloride, and aluminum chloride to a dehydration reaction to obtain an intermediate B having a structure represented by formula (V); wherein Ar₁ and Ar₂ are each independently an aryl group or a substituted aryl group, and formula (V) is as follows:

formula (V)

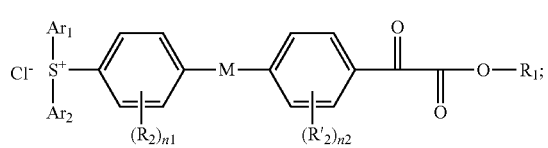

and
subjecting the intermediate B and Y⁻ to an ion exchange reaction to obtain the sulfonium salt photoinitiator.

6. The preparation method according to claim 5, wherein the Friedel-Crafts reaction is performed in the presence of a catalyst and an organic solvent.

7. The preparation method according to claim 6, wherein the Friedel-Crafts reaction is performed at a reaction temperature of 5 to 15° C.

8. The preparation method according to claim 5, wherein the dehydration reaction is performed at a reaction temperature of −5 to 15° C.

9. A photocurable composition comprising a polymerizable monomer and a photoinitiator, wherein the photoinitiator comprises the sulfonium salt photoinitiator of claim 1.

10. The sulfonium salt photoinitiator according to claim 1, wherein M represents O or S.

11. The sulfonium salt photoinitiator according to claim 1, wherein $R_2$ and $R_2'$ are each independently a $C_1$ to $C_5$ linear or branched alkyl group.

12. The sulfonium salt photoinitiator according to claim 3, wherein Q represents O or S.

13. The preparation method according to claim 6, wherein the catalyst is aluminum chloride or zinc chloride.

14. The preparation method according to claim 6, wherein the Friedel-Crafts reaction is performed at a reaction temperature of 5 to 10° C.

15. The preparation method according to claim 6, wherein in the Friedel-Crafts reaction, a molar ratio of the raw material a, the raw material b, and the catalyst is 1:1:1.

16. The preparation method according to claim 5, wherein the dehydration reaction is performed at a reaction temperature of −5 to 5° C.

17. A photocurable composition comprising a polymerizable monomer and a photoinitiator, wherein the photoinitiator comprises the sulfonium salt photoinitiator of claim 2.

18. A photocurable composition comprising a polymerizable monomer and a photoinitiator, wherein the photoinitiator comprises the sulfonium salt photoinitiator of claim 3.

19. A photocurable composition comprising a polymerizable monomer and a photoinitiator, wherein the photoinitiator comprises the sulfonium salt photoinitiator of claim 4.

20. A compound selected from the group consisting of: